(12) United States Patent
Wong et al.

(10) Patent No.: US 9,666,053 B2
(45) Date of Patent: May 30, 2017

(54) DEVICE FOR TAGGING AN OBJECT

(71) Applicant: Hong Kong R&D Centre for Logistics and Supply Chain Management Enabling Technologies Limited, Pok Fu Lam (HK)

(72) Inventors: Kwong Yeung Simon Wong, Pok Fu Lam (HK); Chi Hung Tong, Pok Fu Lam (HK); Chun Wai Lai, Pok Fu Lam (HK); Tsz Ching Anthony Kwok, Pok Fu Lam (HK); Yiu Man Chan, Pok Fu Lam (HK)

(73) Assignee: Hong Kong R&D Centre for Logistics and Supply Chain Management Enabling Technologies Limited, Hong Kong (HK)

( * ) Notice: Subject to any disclaimer, the term of this patent is extended or adjusted under 35 U.S.C. 154(b) by 0 days.

(21) Appl. No.: 14/766,819

(22) PCT Filed: Feb. 8, 2013

(86) PCT No.: PCT/CN2013/071569
§ 371 (c)(1),
(2) Date: Aug. 10, 2015

(87) PCT Pub. No.: WO2014/121517
PCT Pub. Date: Aug. 14, 2014

(65) Prior Publication Data
US 2015/0379850 A1     Dec. 31, 2015

(51) Int. Cl.
*G08B 1/08* (2006.01)
*G08B 21/02* (2006.01)
*A61B 90/90* (2016.01)
*A61B 5/00* (2006.01)
*A61B 90/98* (2016.01)

(52) U.S. Cl.
CPC ........ *G08B 21/0286* (2013.01); *A61B 5/6843* (2013.01); *A61B 90/90* (2016.02); *A61B 5/6824* (2013.01); *A61B 5/6828* (2013.01); *A61B 5/6831* (2013.01); *A61B 90/98* (2016.02); *A61B 2560/0214* (2013.01); *A61B 2562/0214* (2013.01)

(58) Field of Classification Search
None
See application file for complete search history.

(56) References Cited

U.S. PATENT DOCUMENTS 8,410,926 B1   4/2013  Gary, Jr. et al.
2005/0231366 A1 * 10/2005 McHugh ............ G08B 13/1445
                                                      340/568.2

(Continued)

*Primary Examiner* — Adolf DSouza
(74) *Attorney, Agent, or Firm* — Renner Kenner Greive Bobak Taylor & Weber (57) ABSTRACT

A device for tagging an object includes a tag body having an engagement arrangement with a removable strap for engaging the tag body to the object. The engagement arrangement further includes a sensing arrangement having a strap sensor arrv banged to be connected to the removable strap to detect a disengagement of the tag body from the object. The removable strap further includes a conductive member arranged to connect with the strap sensor and disconnect from the strap sensor when the tag body is disengaged from the object.

21 Claims, 6 Drawing Sheets

(56) References Cited

U.S. PATENT DOCUMENTS

2007/0285246 A1* 12/2007 Koyama ................. G06F 1/263
                                                     340/572.1
2010/0162532 A1    7/2010 York
2011/0251498 A1* 10/2011 Nasella .............. A61B 5/02141
                                                     600/490

* cited by examiner

DEVICE FOR TAGGING AN OBJECT

CROSS-REFERENCE TO RELATED APPLICATIONS

This application is a National Phase filing of PCT Application No. PCT/CN2013/071569, filed Feb. 8, 2013, the entirety of which is incorporated herein by reference.

TECHNICAL FIELD

The present invention relates to a device for tagging an object and particularly, although not exclusively, to a tagging device for tagging a patient.

BACKGROUND

In today's hospital, it is common to find a large number of patients undergoing various forms of medical care and treatment of varying durations. Tagging labels are commonly used for identifying these patients as it is important to keep track of each patient to ensure correct medical care or security is administered by the hospital authority and medical staff. These labels are usually provided with barcodes and text so that the label may be read or scanned by a barcode scanner. These labels are usually tided on the wrist of the patient, or simply attached to the patient with adhesives.

One such use includes the attachment of these labels to new born infants. The text labels provide an easier solution for identifying a large number of babies, which may each look very similar when placed in a nursery.

Baby abduction and its immense consequences have occurred to arouse public concern. It is common that new born babies travel frequently to different rooms within a hospital for health checking and nursing, and thus these general movements by different medical personnel may expose the infants to risks of abduction. Simple text labels attached to the babies' wrist could be easily detached from the babies either by accident, or intentionally whilst being completely silent without the provision of alerts, to the guardian of the infant. In addition, these tagging labels are basically not resistant to tamper which increases the risk of baby abduction.

SUMMARY

In accordance with a first aspect of the present invention, there is provided a device for tagging an object comprising: a tag body having an engagement arrangement for engaging the tag body to the object, wherein the engagement arrangement includes at least one sensing arrangement arranged to detect a disengagement of the tag body from the object.

In an embodiment of the first aspect, the at least one sensing arrangement is arranged to detect a manipulation with the engagement arrangement.

In an embodiment of the first aspect, the manipulation to the engagement arrangement includes removing, disengaging or damaging the engagement arrangement.

In an embodiment of the first aspect, the engagement arrangement includes a cuff member arranged to engage with a limb of the object.

In an embodiment of the first aspect, the cuff member is defined by a substantially C-shaped collar arranged to fit snugly with the limb of the object to engage the tag body to the object.

In another embodiment, the cuff member defined by a O-shaped cuff, U-shaped cuff or another shape or form arranged to engage with a limb of an object or user. Preferably, the cuff can also be made from a range of material including elastic, flexible and soft materials such as silicone or plastics.

In an embodiment of the first aspect, the sensing arrangement includes a cuff sensor disposed adjacent to the cuff, the cuff sensor arranged to detect a disengagement of the cuff from the limb of the object.

In an embodiment of the first aspect, at least one portion of the cuff sensor is integrally formed within the cuff member.

In an embodiment of the first aspect, the cuff sensor includes a conductive sheet arranged to detect the disengagement of the cuff from the limb of the object.

In an embodiment of the first aspect, the conductive sheet is integrated into the cuff member.

In an embodiment of the first aspect, the engagement arrangement includes a removable strap for engaging the tag body to the object.

In an embodiment of the first aspect, wherein the sensing arrangement includes a strap sensor arranged to be connected to the removable strap to detect the disengagement of the tag body from the object.

In an embodiment of the first aspect, wherein the removable strap includes a conductive member arranged to connect with the strap sensor.

In an embodiment of the first aspect, the conductive member is arranged to disconnect from the strap sensor when the tag body is disengaged from the object.

In an embodiment of the first aspect, the strap sensor is arranged to detect a disconnection between the conductive member and the strap sensor.

In an embodiment of the first aspect, the tag body further includes a RFID arrangement for communicating with a RFID system.

In an embodiment of the first aspect, the RFID arrangement includes an active RFID circuit.

In an embodiment of the first aspect, the tag body further includes a wireless charging system.

In an embodiment of the first aspect, the RFID arrangement is arranged to transmit a signal to the RFID system when the sensing arrangement senses the disengagement of the tag body from the object.

In an embodiment of the first aspect, the RFID arrangement is housed within the tag body.

In an embodiment of the first aspect, the device is arranged to be engaged to a limb of a new born infant.

In accordance with a second aspect of the present invention, there is provided a method for tagging an infant comprising the steps of engaging a tagging device in accordance with any one embodiment of the first aspect to a limb of the infant.

In accordance with a third aspect of the present invention, there is provided a wireless communication device comprising a housing arranged to house a communication module, a cuff member to detect engagement of the wireless communication device from an object, a strap to detect damage of the wireless communication device, wherein the strap arranged to substantially support the cuff.

In accordance with a forth aspect of the present invention, there is provided a wireless communication device comprising a housing arranged to house a communication module, a strap to detect engagement of the wireless communication device from an object and damage of the wireless communication device.

In a wireless communication device in accordance with any one embodiment of the third aspect or the forth aspect, the communication module includes an RFID circuits arranged to communicate with an RFID system.

In a wireless communication device in accordance with any one embodiment of the third aspect or the forth aspect, the wireless communication device further comprising a wireless charging system arranged to recharge a rechargeable battery.

BRIEF DESCRIPTION OF THE DRAWINGS

Embodiments of the present invention will now be described, by way of example, with reference to the accompanying drawings in which.

DETAILED DESCRIPTION OF THE PREFERRED EMBODIMENT

Figure 1:
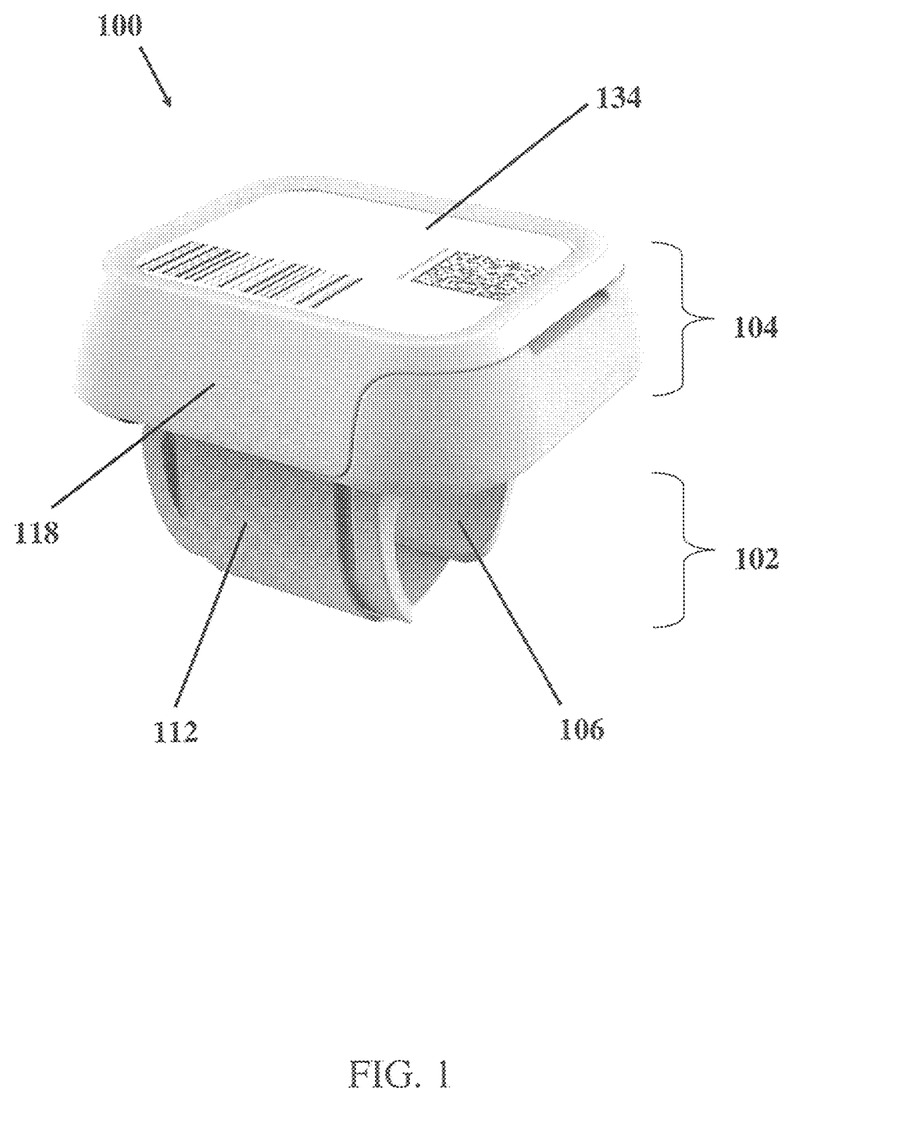
FIG. 1 is a perspective view of a device for tagging an object in accordance with an embodiment of the present invention.
Figure 2:
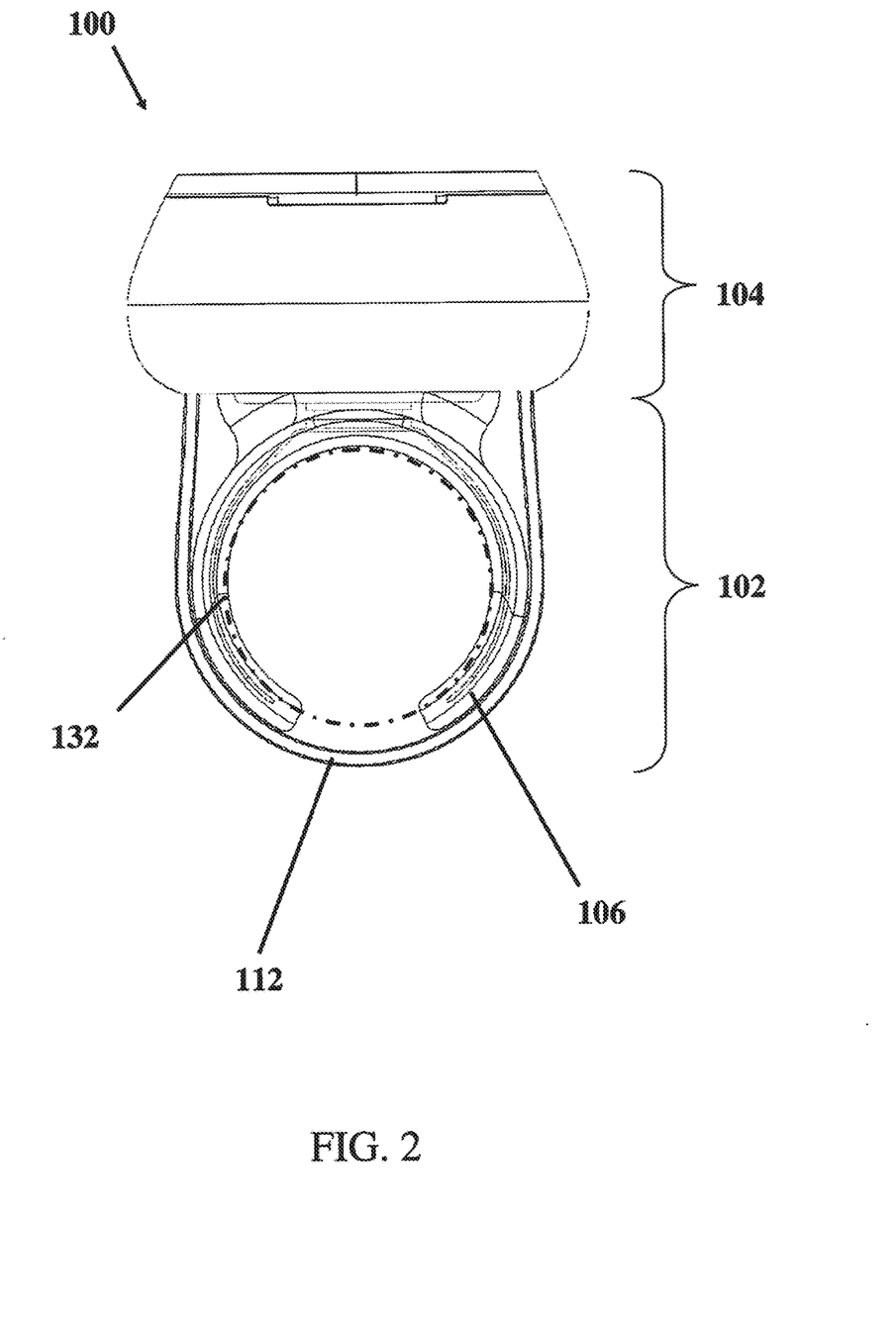
FIG. 2 is a side view of a device of FIG. 1.

Referring to FIGS. 1 and 2, there is provided an embodiment of a device for tagging an object comprising: a tag body having an engagement arrangement for engaging the tag body to the object, wherein the engagement arrangement includes at least one sensing arrangement arranged to detect a disengagement of the tag body from the object.

Figure 3:
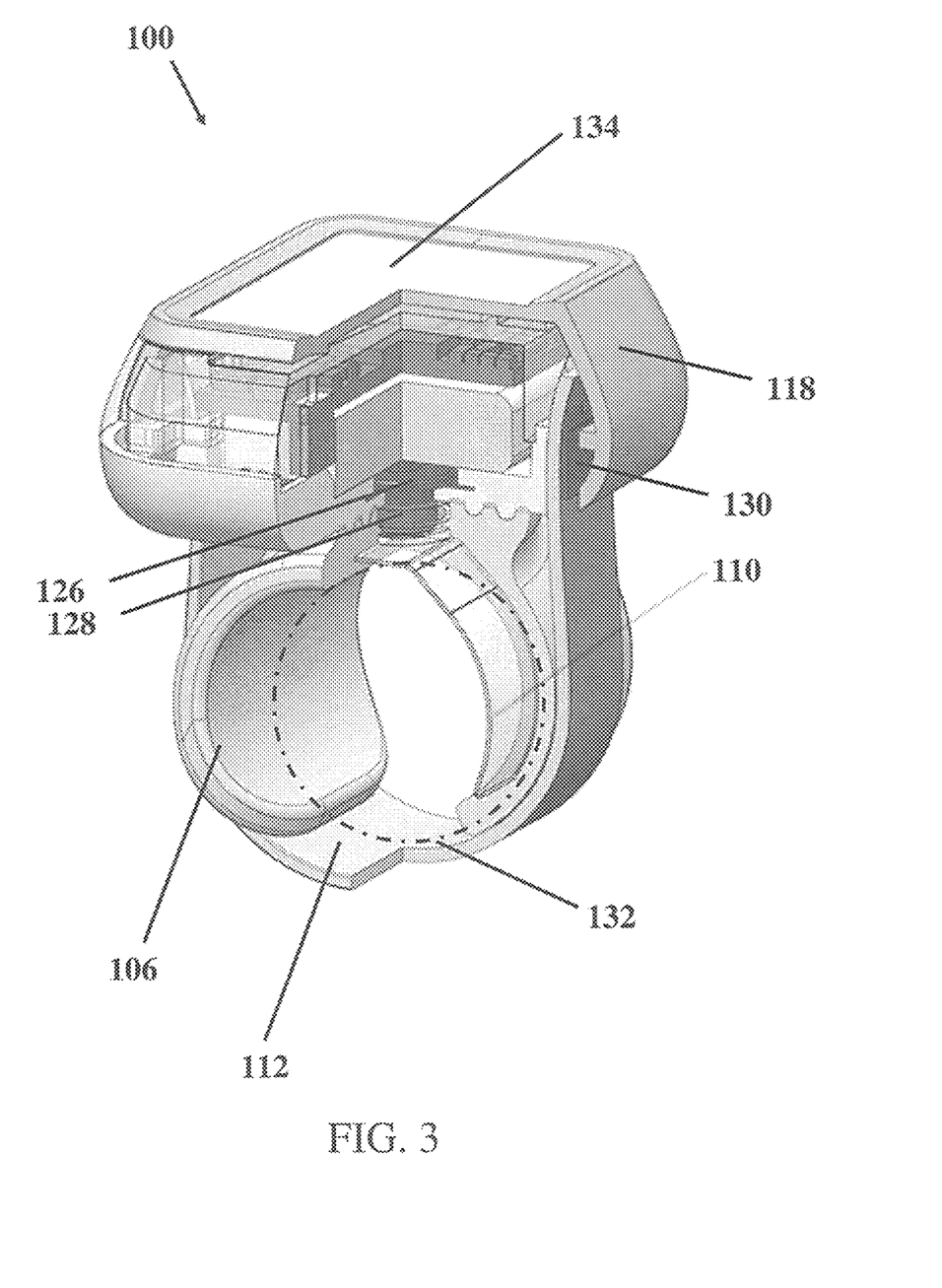
FIG. 3 is a cross sectional view of a device of FIG. 1.
Figure 4:
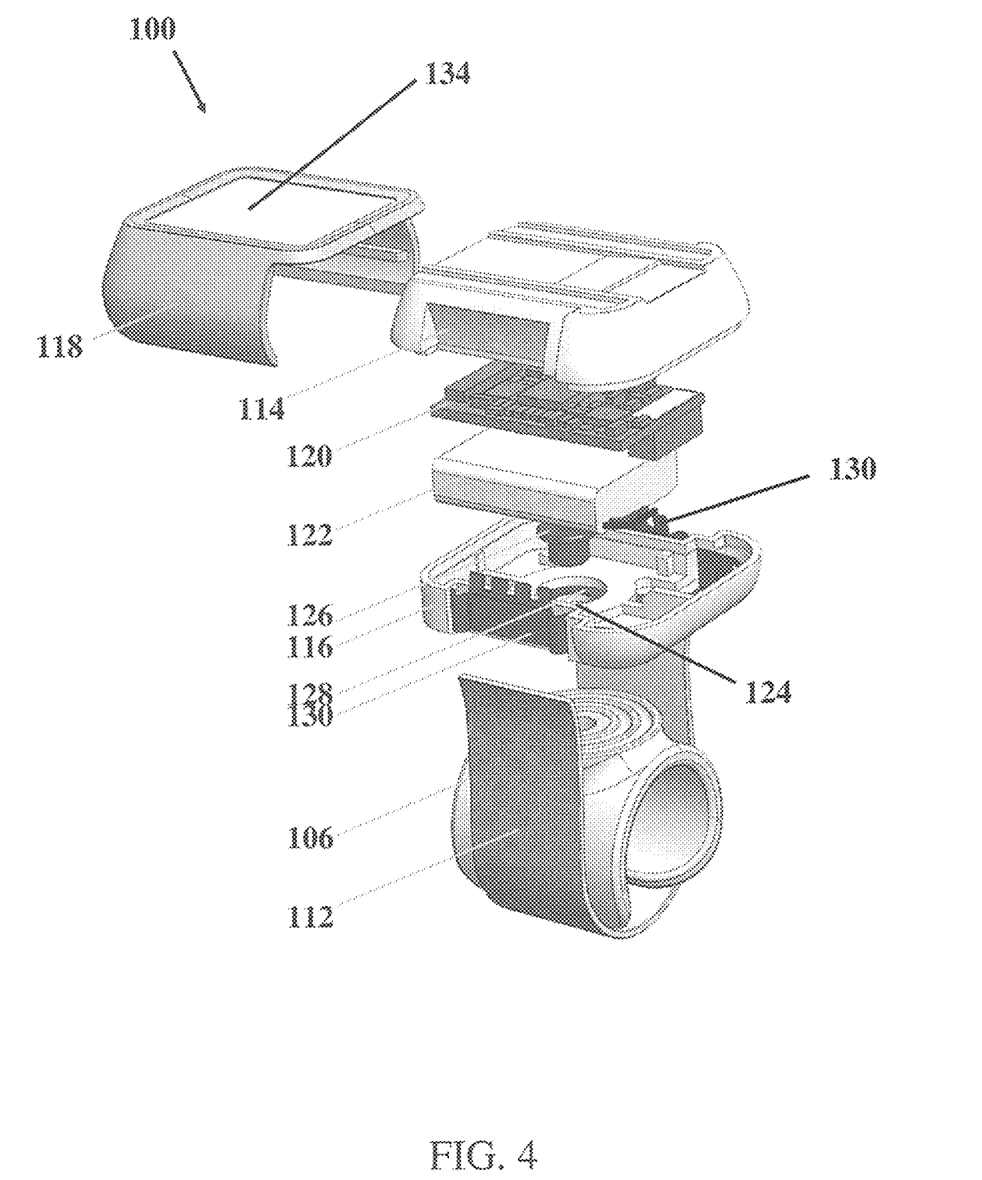
FIG. 4 is an exploded view of a device of FIG. 1.

In this embodiment, the device 100 for tagging an object includes an engagement arrangement 102 and a tag body 104. The engagement arrangement 102 includes two components arranged to engage the device 100 to a limb of an object. As shown in FIGS. 3 and 4, the engagement arrangement 102 includes a cuff member 106 and a removable strap 112. Preferably, the cuff member 106 is defined by a substantially C-shaped collar arranged to fit snugly with the limb of an object, such as the wrist, arm, ankle or leg of a patient. Alternatively the cuff member may be of any shape that fits with the limb of an object, including but not limited to U-shaped and O-Shaped.

In addition, the cuff member may include at least one sensing arrangement. In one example, the sensing arrangement is arranged to employ the capacitive coupling which takes human body capacitance as an input. In this example, the sensing arrangement is configured to detect a human body that has a dielectric constant different from that of air. This sensing arrangement may include a conductive sheet 110 for electrically connecting a human body skin to the tag body 104.

Preferably, the sensing arrangement uses capacitive sensing system whereby the conductive sheet 100 and the cuff member 106 together forms a weak capacitor. As the cuff member 106, which may compose of an insulating material with a dielectric constant, whereupon the conductive sheet 110 is integrated within the cuff member 106, the arrangement forms a capacitor of which its capacitance is altered when a limb of an object, such as a patient's wrist, arm, ankle or leg is attached to the cuff member 106 which has a different dielectric constant to the cuff member 106. By detecting or sensing this change in capacitance, the sensing arrangement is able to sense the engagement of the device 100 to the object.

Alternatively the at least one sensing arrangement may includes a cuff sensor or any other sensor arranged to detect a disengagement of the cuff from the limb of an object.

Preferably the cuff member 106 is made of a flexible material such as, but not limited to, rubber and silicone. Other materials such as plastic, metal etc may also be used to manufacture the cuff member 106 without deviating from the spirit of the invention. Additionally, the at least one portion of the sensing arrangement may be integrally formed within the cuff member.

The engagement arrangement 102 may further include a removable strap 112 for engaging the tag body 104 to an object. The removable strap 112 is preferably positioned at the outer surface of the cuff member 106 arranged to provide support to the cuff member 106 in engaging with the limb of an object.

The sensing arrangement further includes a strap sensor to be connected to the strap 112 to detect the disengagement of the tag body from an object. Preferably, the removable strap 112 includes a conductive member arranged to connect with the strap sensor. Alternatively, the conductive member is integrally formed within the strap 112, and alternatively, the strap 112 can be made with electrically conductive materials.

Referring to FIG. 4, the tag body 104 includes an upper shell coupled to a lower shell 116 which form a housing to house various components, such as a PCB 120, a battery 122, and a tighten nut 126, within the housing. A lock shell 118 is arranged to secure the position of the upper shell and the lower shell 116.

The tag body 104 further includes a printed circuit board (PCB) 120 arrange for mounting electronic components and circuits, which include an RFID arrangement for communicating with an RFID system, any other suitable communication module, such as Wi-Fi, Bluetooth, infra-red, may be mounted on the PCB 120 for communication. Preferably the RFID arrangement includes an active RFID circuit. The tag body 104 may further include a battery 122 arranged to provide electrical power to various components of the device 100. This battery may be a single use battery although preferably the battery 122 is rechargeable. A wireless charging system such as an inductive charging module may also be included to recharge the battery 122 wirelessly. Alternatively, the tag body 104 may include a charging port for recharging the device 100 with a cabled recharger.

The lower shell 116 includes an opening 124 arranged to receive a portion of a tighten nut 126. In this embodiment, the tighten nut 126 penetrate through the opening 124 of the lower shell 116 and is coupled to the cuff member 106. As a result of this arrangement, the cuff member 106 is securely fixed to the tag body. A conductive ring 128 positioned in the opening 124 of the lower shell arranged to electrically connect the conductive sheet 110 or the at least one sensing arrangement to the PCB 120 such that electrical signal is configured to be transmitted from the cuff member 106 to the PCB 120 inside the housing.

As shown in this example, the lower shell further includes at least one spring fastener 130 arranged to move within a first limiting position and a second limiting position. The spring fastener 130 is coupled to the removable strap 112 such that a substantially close loop 132 is formed for engaging a limb of an object through the loop 132. In particular, when the spring fastener 130 is in the second limiting position, the loop 132 is substantially larger than that when the spring fastener 130 is in the first limiting position.

Figure 6:
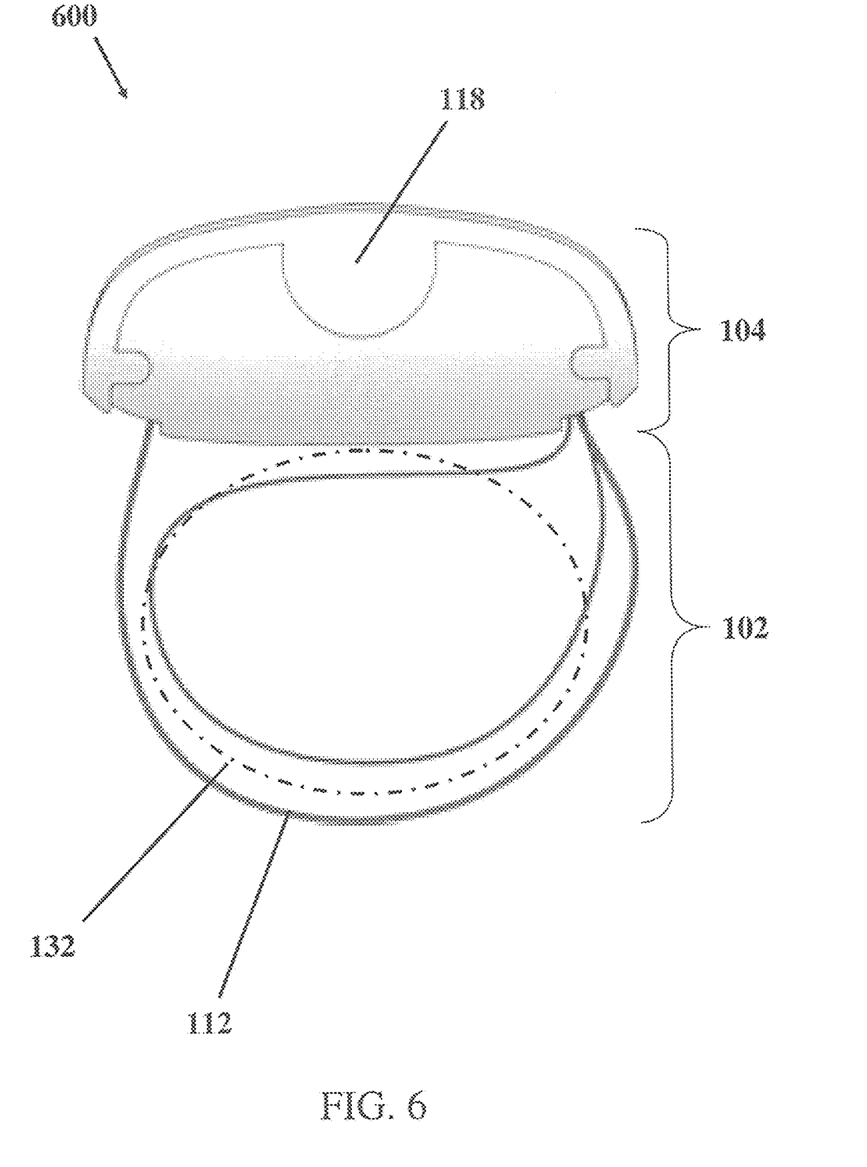
FIG. 6 is a perspective view of a device for tagging an object in accordance with another embodiment of the present invention.

Referring to FIG. 6, there is provided another embodiment of a device for tagging an object comprising a tag body having an engagement arrangement for engaging the tag body to the object, wherein the engagement arrangement includes at least one sensing arrangement arranged to detect a disengagement of the tag body from the object.

In this embodiment, the device 600 for tagging an object includes an engagement arrangement 102 and a tag body 104. As shown in FIG. 6, the engagement arrangement 102 includes a removable strap 112 for engaging the tag body 104 to an object. In this example, the removable strap 112 is arranged to wrap around a limb of an object (such as the arm, wrist, ankle or leg of a person) and can be tightened by adjusting the slack of the strap around the limb to form a snug fit with the limb. In a similar manner, the removable strap 112 is connected to or part of, a sensing arrangement arranged to detect the tampering or disengagement of the device 600 from the limb of the object by capacitive sensing or other forms of sensing arrangement.

Active RFID is a solution in logistics and supply chain management and is adopted to be used in the hospital environment to eliminate the risk of baby abduction.

These embodiments are advantageous in that the position of the sensors as shown in at least one embodiment is able to operate in a more sensitive manner with less error than the placement of sensors in other parts of the tag, such as in the housing or at a surface of the housing, and is thus less prone to false alarm. These embodiments are also advantageous in that the engagement arrangement is resistant to tamper, so as to further reduce the risks of abduction, when compared to simple straps without a strap sensor.

An example embodiment of the device 100 for tagging a new born infant with reference to FIGS. 1 to 5 is provided below. In the first instance, the loop 132 can be enlarged by pulling the strap 112 such that the at least one spring fastener move from the first limiting position to the second limiting position, then the device 100 can be engaged to a limb of a new born infant through the loop 132, by releasing the spring fastener back to the first limiting position, the loop 132 restore to a smaller dimension. As a result the strap 112 applies an inward supportive force to the cuff member 106, such that the inner wall of the cuff member 106 attaches firmly to the skin of the limb of the new born infant, and the attachment is detected by the conductive sheet 110 on the cuff member 106. The flexible C-shaped collar structure helps to improve the attachment of the cuff member 106 to the skin of the limb and hence improve the accuracy of the detection of the cuff sensor over an O-shaped collar design.

When the tag body 104 is disengaged from the limb of the new born infant, the conductive member of the strap 112 is arranged to disconnect from the strap sensor, and the disconnection between the conductive member and the strap sensor is detected by the strap sensor. In addition, the detachment of the cuff member 106 from the skin of the limb of the new born infant is detected by the cuff sensor.

Figure 5:
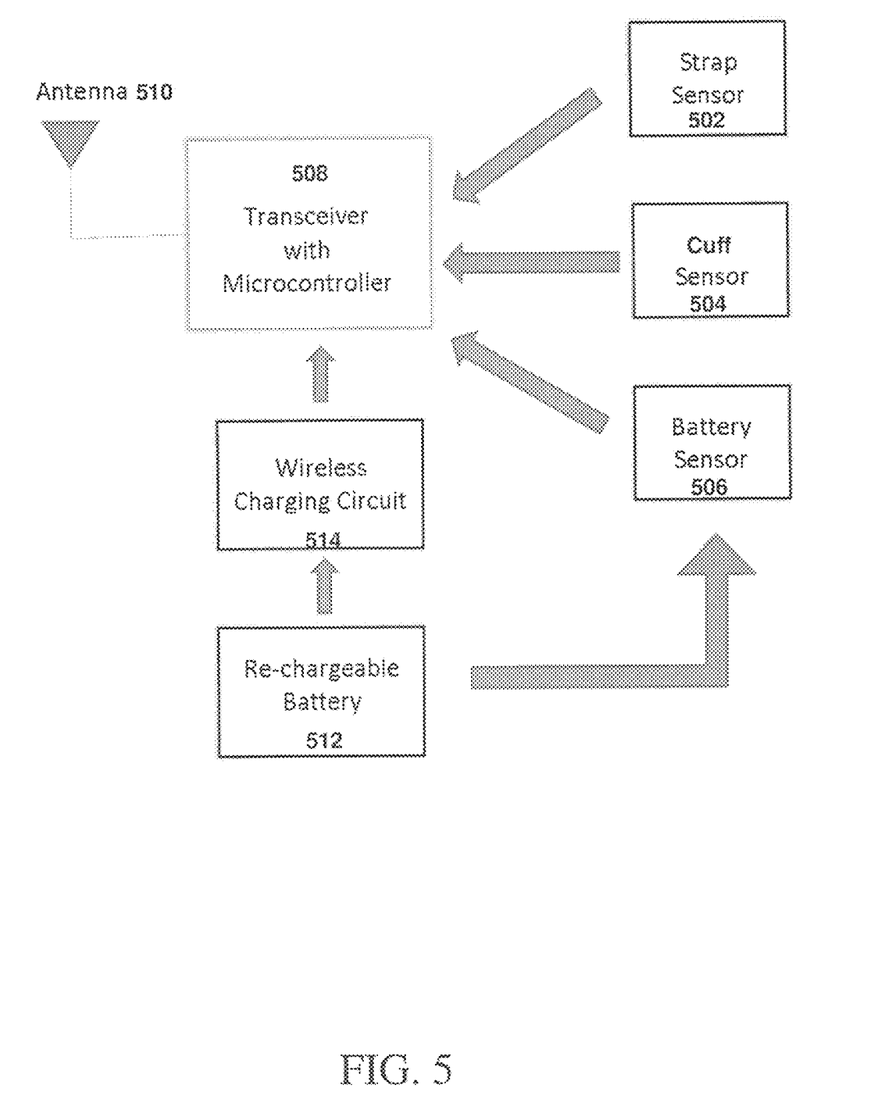
FIG. 5 is a block diagram of the operation of the device of FIG. 1.

Referring to FIG. 5, when the tagging device 100 and the RFID system (not shown) are in operation, the tag body 104 is arranged to process the sensing signal fed from the strap sensor 502, the cuff sensor 504 (which may be capacitive and the battery sensor 506. Upon a manipulation to the engagement arrangement, which includes removing the attached device from the skin, disengaging the engaged device from the limb, and damaging of the strap 112, is detected by any of the sensing arrangement, a detection signal will be processed by a transceiver with a microcontroller 508 and the active RFID circuit will transmit a signal via an antenna 510 to the RFID system which can alert a user of the tagging device. In addition, the battery sensor 506 is arranged to detect the operating voltage of the battery such that the active RFID circuit can transmit a signal to the RFID system to alert a user when the battery level becomes low and requires attention such as recharging the battery 512 with a charging circuit 514.

On the top surface 134 of the lock shell 118, a user can write or label information including text, images, symbols, barcodes or any combination thereof, to help identifying the tagging device or the object with the device engaged.

Without deviating from the spirit of the invention, the tagging device can be engaged to any limb of a living creature or any object. In some embodiments, the tag can be arranged for engagement to an object other than an infant for tagging or tracking of the object. These objects may include adult or child patients, animals or inanimate objects such as bodies, animal carcasses, furniture, vehicles, etc.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

Any reference to prior art contained herein is not to be taken as an admission that the information is common general knowledge, unless otherwise indicated.

The invention claimed is:

1. A device for tagging an object comprising:
 a tag body having an engagement arrangement with a removable strap for engaging the tag body to the object, wherein the engagement arrangement further includes at least one sensing arrangement having a strap sensor arranged to be connected to the removable strap to detect a disengagement of the tag body from the object, wherein the removable strap includes a conductive member arranged to connect with the strap sensor and disconnect from the strap sensor when the tag body is disengaged from the object.

2. A device in accordance with claim 1, wherein the at least one sensing arrangement is arranged to detect a manipulation with the engagement arrangement.

3. A device in accordance with claim 1, wherein the manipulation to the engagement arrangement includes removing, disengaging or damaging the engagement arrangement.

4. A device in accordance with claim 1, wherein the engagement arrangement includes a cuff member arranged to engage with a limb of the object.

5. A device in accordance with claim 4, wherein the cuff member is defined by a substantially C-shaped collar arranged to fit snugly with the limb of the object to engage the tag body to the object.

6. A device in accordance with claim 4, wherein the sensing arrangement includes a cuff sensor disposed adjacent to the cuff, the cuff sensor arranged to detect a disengagement of the cuff from the limb of the object.

7. A device in accordance with claim 6, wherein at least one portion of the cuff sensor is integrally formed within the cuff member.

8. A device in accordance with claim 6, wherein the cuff sensor includes a conductive sheet arranged to detect the disengagement of the cuff from the limb of the object.

9. A device in accordance with claim 8, wherein the conductive sheet is integrated into the cuff member.

10. A device in accordance with claim 1, wherein the strap sensor is arranged to detect a disconnection between the conductive member and the strap sensor.

11. A device in accordance with claim 1, wherein the tag body further includes a RFID arrangement for communicating with a RFID system.

12. A device in accordance with claim 11, wherein the RFID arrangement includes an active RFID circuit.

13. A device in accordance with claim 11, further including a wireless charging system.

14. A device in accordance with claim 11, wherein the RFID arrangement is arranged to transmit a signal to the RFID system when the sensing arrangement senses the disengagement of the tag body from the object.

15. A device in accordance with claim 11, wherein the RFID arrangement is housed within the tag body.

16. A wireless communication device in accordance with claim 14, wherein the communication module includes an RFID circuit arranged to communicate with an RFID system.

17. A wireless communication device in accordance with claim 14, further comprising a wireless charging system arranged to recharge a rechargeable battery.

18. A device in accordance with claim 1 arranged to be engaged to a limb of a new born infant.

19. A method for tagging an infant comprising the step of engaging a tagging device in accordance with claim 1 to a limb of the infant.

20. A wireless communication device comprising: a tag body; a housing arranged to house a communication module; a cuff member to detect engagement of the wireless communication device with an object; a removable strap to detect damage of the wireless communication device; and a strap sensor arranged to be connected to the removable strap to detect a disengagement of the tag body from the object, wherein the removable strap is arranged to substantially support the cuff, and the removable strap includes a conductive member arranged to connect with the strap sensor and disconnect from the strap sensor when the tag body is disengaged from the object.

21. A wireless communication device comprising: a tag body; a housing arranged to house a communication module; a removable strap to detect engagement of the wireless communication device with an object and detect damage of the wireless communication device; and a strap sensor arranged to be connected to the removable strap to detect a disengagement of the tag body from the object, wherein the removable strap includes a conductive member arranged to connect with the strap sensor and disconnect from the strap sensor when the tag body is disengaged from the object.

* * * * *